United States Patent [19]

Cazal

[11] Patent Number: 5,800,414
[45] Date of Patent: Sep. 1, 1998

[54] CATHETER WITH FLEXIBLE AND ELONGATE BODY

[75] Inventor: Thierry Cazal, Sarlat, France

[73] Assignee: Synthelabo, Le Plessis Robinson, France

[21] Appl. No.: 924,140

[22] Filed: Sep. 5, 1997

[30] Foreign Application Priority Data

Oct. 18, 1996 [FR] France ............... 96 12687

[51] Int. Cl.⁶ .................................. A61M 25/00
[52] U.S. Cl. .................................. 604/280; 604/264
[58] Field of Search .................. 604/280, 264, 604/43, 53, 283, 284

[56] References Cited

U.S. PATENT DOCUMENTS

| 4,306,562 | 12/1981 | Osborne ............... 604/280 |
| 4,402,685 | 9/1983 | Buhler et al. ............... 604/280 |
| 4,692,153 | 9/1987 | Berlin et al. ............... 604/280 X |
| 5,195,978 | 3/1993 | Schiffer ............... 604/280 X |
| 5,695,457 | 12/1997 | St. Goar et al. ............... 604/53 X |

FOREIGN PATENT DOCUMENTS 0 332 366 A2  9/1989  European Pat. Off.
2 156 033  10/1985  United Kingdom.

*Primary Examiner*—John D. Yasko
*Attorney, Agent, or Firm*—Fisher, Christen & Sabol

[57] ABSTRACT

The present invention relates to a medical or surgical probe.

According to the invention:

- the elongate body (2) of said probe includes a central longitudinal channel (4) delimiting, within said body, longitudinal portions (5, 6) connected to one another by surface material lines (8) which are easily tearable;
- each of said longitudinal portions of the body includes an internal longitudinal conduit (9, 10);
- each of the branches (11, 12) of the probe is formed by one such longitudinal portion of said body, separated from the other longitudinal portion; and
- the cross section of said longitudinal channel (4) is capable of receiving a tubular element.

6 Claims, 2 Drawing Sheets

CATHETER WITH FLEXIBLE AND ELONGATE BODY

The present invention relates to a probe or catheter generally used in medicine or in surgery, particularly in urodynamics or in the cardiovascular field. Such probes are used for measuring pressure and flow rate or for transmission of liquids, for example in the bladder, urethra, etc.

The present invention relates in a general manner to a medical or surgical probe of known type, intended to be introduced into a body passage and provided with at least two individual longitudinal channels, each extending between the proximal end and the distal end of said probe, this probe including:

a flexible and elongate body intended to be introduced via its distal end into said body passage and provided with at least two internal longitudinal conduits; and at least two flexible and elongate proximal branches which are each provided with an internal longitudinal conduit and are arranged at the proximal end of said elongate body, each of the conduits of said branches continuing a conduit of said elongate body in order to form one of said individual longitudinal channels of said probe.

Thus, each of said channels, which opens to the outside of the probe at the proximal and distal ends thereof, either via lateral orifices, or via end orifices, can be used for transmission of fluid and/or pressure.

The production of such probes is complex and costly. This is because it is necessary to join said branches to one another and to said flexible and elongate body, in such a way that the conduit of each branch is in continuous sealed communication with a conduit of said flexible and elongate body and with this conduit alone.

This entails complex adhesive bonding, welding or overmolding operations. The result of this is that the cost of these known probes is high, all the more so as the number of longitudinal channels increases.

The present invention aims to overcome these disadvantages and it relates to a probe which, while it can be produced at low cost, makes it possible to easily obtain a supplementary longitudinal conduit compared to the number of the branches.

To this end, according to the invention, the medical or surgical probe of the type mentioned above is distinguished by the fact that:

said flexible and elongate body includes, in addition to said internal longitudinal conduits, a central longitudinal channel delimiting, within said body, longitudinal portions connected to one another by surface material lines, which are easily tearable;

each of said longitudinal portions of the body includes one of said internal longitudinal conduits;

each of said proximal branches is formed by one such longitudinal portion of said body, separated from said other longitudinal portions, over a limited length, along said tearable surface material lines; and said central longitudinal channel has a cross section which is capable of receiving a tubular element which can be attached to said elongate body, at the junction of said proximal branches of said probe.

Thus, each of said proximal branches can be formed by separation of said longitudinal portions, in the way one peels a banana. Each of the proximal branches is for this reason made up of a longitudinal portion of the flexible and elongate body, and each conduit of the latter constitutes the conduit of a proximal branch. In terms of construction, each conduit of a proximal branch is thus the continuation of a specific conduit of the flexible and elongate body, so as to form an individual longitudinal channel. There is therefore no need for connecting the proximal branches to the body and connecting the conduits of said branches to the conduits of said body. It will be readily appreciated that said body can be produced at low cost by extrusion of synthetic material.

Furthermore, in the part of the body where said longitudinal portions are not separated from one another to form said proximal branches, it will be readily seen that said central longitudinal channel can be used as a supplementary individual longitudinal channel, optionally continued on the proximal side of the probe via said tubular element.

It will be noted that the document EP-A-0332366 describes a drainage device which includes at least two individual distal conduits connected in common, via a collector, to a single common drainage conduit leading to the proximal end of said drainage device, said distal conduits being obtained by longitudinal separation of a multi-conduit profile in which said conduits are juxtaposed and connected to one another via a tearable longitudinal wall. To facilitate the separation of said distal conduits, an internal slot is made in this tearable longitudinal wall in such a way as to leave only two tearable connecting lines at the periphery of said connecting wall.

Thus, this known drainage device is not made up of a single piece between its proximal end and its distal end. On the contrary, it is formed by assembling independent components, namely the distal conduits, the collector and the common proximal conduit. It will be noted that such assembly does not cause any difficulty either, even if the number of distal conduits is high, since each individual distal conduit does not have to extend over the whole of the drainage device, but only between the distal end thereof and said collector, and since the individual distal conduits are connected in common to the common drainage conduit via the collector. There is therefore no need to connect each distal conduit extensively and specifically to another individual conduit. Furthermore, it is obvious that, because of its flattened shape, the slot within said tearable longitudinal wall cannot play any part in the drainage under conditions comparable to those of said distal conduits.

In order to avoid the separation of said proximal branches of the probe according to the invention propagating excessively along said body, said proximal branches are preferably joined to one another at their junction by joining means, for example by adhesive bonding or by fitting of a ring.

Such joining means can furthermore join said tubular element to said probe.

As will be seen hereinafter, with reference to the figures, said elongate body may include a number of longitudinal portions which is greater than two, for example three or four. Depending on the number of said longitudinal portions, the cross section of said central longitudinal channel may then have the approximate shape of a lens, a triangle or a square, respectively.

From the figures in the attached drawing, it will be readily understood how the invention can be realized. In these figures, identical reference labels designate similar elements.

Figure 1:
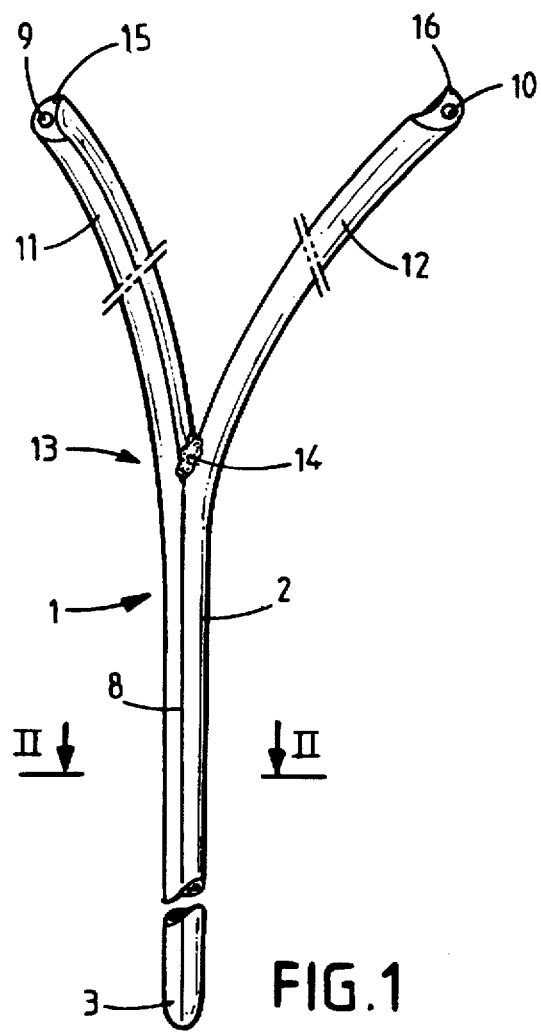
FIG. 1 is a diagrammatic and simplified representation of a probe according to the present invention.
Figure 2:
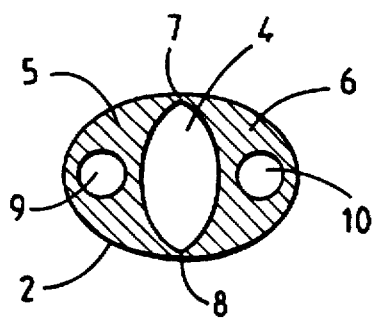
FIG. 2 is a cross section along the line II—II in FIG. 1.

The probe 1 shown diagrammatically in FIGS. 1 and 2 includes a flexible and elongate body 2 intended to be introduced via its distal end 3 into a body passage. As is shown more particularly in FIG. 2, the elongate body 2 includes a central longitudinal channel 4 delimiting, within said body, longitudinal portions 5 and 6 which are connected to one another by surface material lines 7 and 8, which are easily tearable. In the example shown, the longitudinal channel 4 presents the shape of a biconvex lens, while said longitudinal portions 5, 6 have the shape of crescents which are connected via their tips along the tearable lines 7 and 8. Each of said longitudinal portions 5 and 6 includes an internal longitudinal conduit 9 or 10.

Toward its proximal end, the probe includes two branches 11 and 12, formed respectively by the proximal parts of the longitudinal portions 5 and 6, separated from one another by tearing the lines 7 and 8 over a limited length.

At the junction 13 of the proximal branches 11 and 12 on the elongate body 2, said branches 11 and 12 are joined to one another, for example by adhesive 14.

Of course, the proximal ends 15 and 16 of the branches 11 and 12 can be provided in the usual way with cannulas (not shown). It will be noted that the internal longitudinal conduits 9 and 10 form individual channels, each extending between the proximal end and the distal end of the probe 1.

Figure 3:
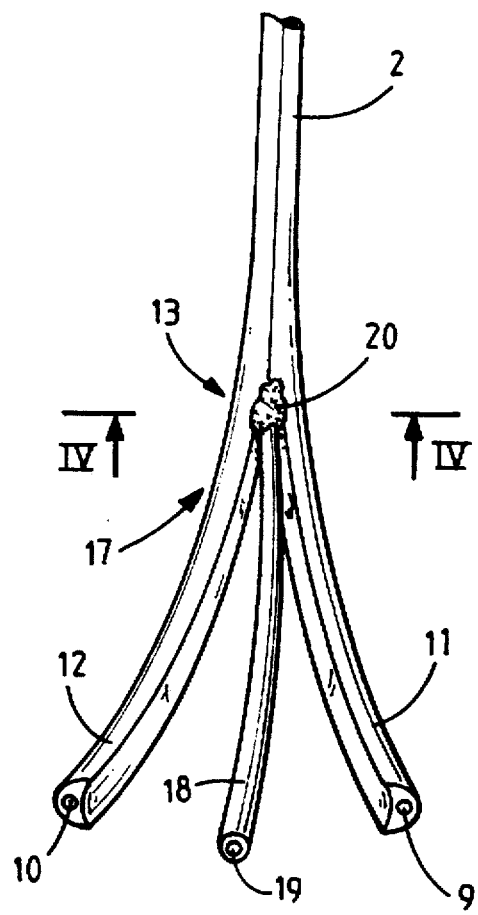
FIG. 3 illustrates, in a view similar to FIG. 1, an alternative embodiment of the probe according to the present invention.
Figure 4:
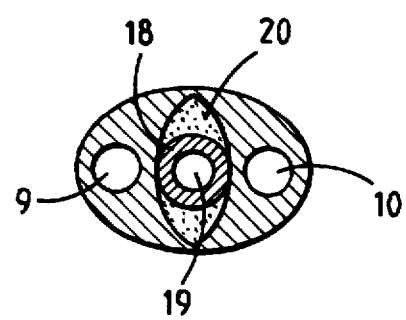
FIG. 4 is a cross section along the line IV—IV in FIG. 3, at the area of the junction of the branches on the elongate body.

As is illustrated by FIGS. 3 and 4, it is possible to obtain, starting from the probe 1 in FIGS. 1 and 2, a probe 17 which has three branches. The third branch is formed by a tubular element 18, one end of which is embedded in the channel 4, in the area of the junction 13. Thus, the conduit 19 of the tubular element 18 is in fluid communication with said central longitudinal channel 4. The tubular element 18 can be fixed to the body 2 by adhesive 20 joining its external wall to the wall of the longitudinal channel 4. In this case, the adhesive 20 also joins the proximal branches 11 and 12 to one another.

Figure 5:
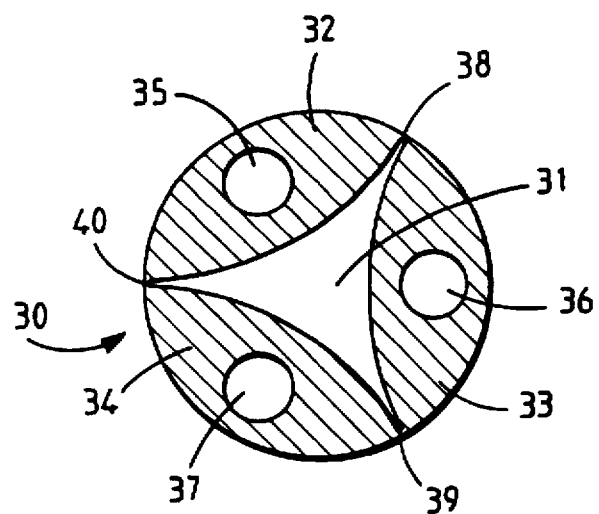
FIG. 5 shows, in cross section, an alternative embodiment of the body of the probe according to the present invention, this body comprising three longitudinal portions.
Figure 6:
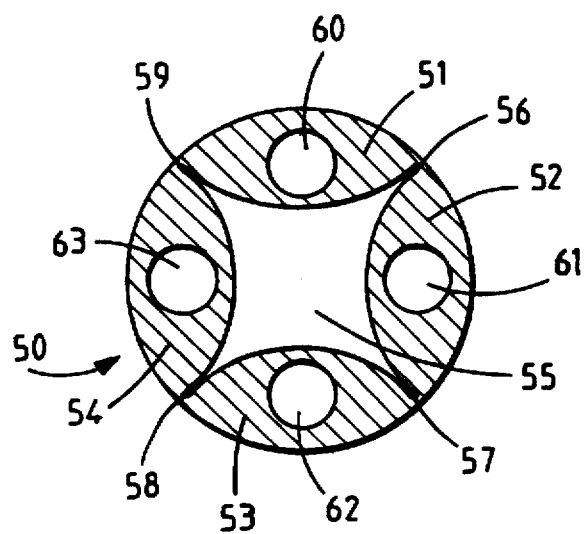
FIG. 6 shows, also in cross section, another alternative of the elongate body of the probe according to the present invention, this body comprising four longitudinal portions.

FIGS. 5 and 6 illustrate, in cross section comparable to FIG. 2, alternative embodiments of the probe according to the present invention.

FIG. 5 shows a body 30 (similar to the body 2) including a central longitudinal channel 31 (comparable to the central longitudinal channel 4) delimiting, within said body 30, three longitudinal portions 32, 33 and 34 (comparable to the longitudinal portions 5 and 6), each being provided with an internal longitudinal conduit 35, 36 and 37 (comparable to the conduits 9 and 10).

In this embodiment, the central longitudinal channel 31 presents, in cross section, the shape of a triangle with concave curvilinear sides, while the longitudinal portions 32, 33 and 34 present the shape of biconvex lenses which are connected to one another via surface material lines 38, 39 and 40, which are easily tearable. It will be readily appreciated that the flexible and elongate body 30 can easily form three branches (comparable to the branches 11 and 12), by separating said longitudinal portions 32, 33 and 34 along a limited part of the lines 38, 39 and 40, at the proximal end of the probe 30.

In the embodiment 50 in FIG. 6, there are four longitudinal portions 51, 52, 53 and 54, which can give rise to four branches similar to the branches 11 and 12.

In this embodiment 50, the central longitudinal channel 55 presents the shape of a square with concave curvilinear sides, while each of the portions 51, 52, 53 and 54 presents the shape of a biconvex lens, these lenses being connected to one another by easily tearable surface lines 56, 57, 58 and 59. The longitudinal portions 51 to 54 each include a longitudinal conduit 60 to 63.

The probe formed by the body 50 can of course include four branches similar to the branches 11 and 12, formed respectively by separating, over a limited length, the longitudinal portions 51, 52, 53 and 54 along the lines 56 to 59.

It will be noted that in the embodiments in FIGS. 5 and 6, it is possible to provide a supplementary branch by introducing a tubular element 18 into the central longitudinal channel 31 or 55. it will also be noted that the flexible and elongate bodies 2, 30 and 50 can easily be obtained, at low cost, by extrusion of a synthetic material.

I claim:

1. A medical or surgical probe, intended to be introduced into a body passage and provided with at least two individual longitudinal channels, each extending between the proximal end and the distal end of said probe, this probe including:

a flexible and elongate body (2, 30, 50) intended to be introduced via its distal end (3) into said body passage and provided with at least two internal longitudinal conduits (9, 10; 35, 36, 37; 60, 61, 62, 63); and at least two flexible and elongate proximal branches (11, 12) which are each provided with an internal longitudinal conduit (9, 10) and are arranged at the proximal end of said elongate body, each of the conduits of said branches continuing a conduit of said elongate body in order to form one of said individual longitudinal channels of said probe, wherein:

said flexible and elongate body (2, 30, 50) includes, in addition to said internal longitudinal conduits, a central longitudinal channel (4, 31, 55) delimiting, within said body, longitudinal portions (5, 6; 32, 33, 34; 51, 52, 53, 54) connected to one another by surface material lines, which are easily tearable open;

each of said longitudinal portions of the body includes one of said internal longitudinal conduits (9, 10; 35, 36, 37; 60, 61, 62, 63);

each of said proximal branches (11, 12) is formed by one such longitudinal portion of said body, separated from said other longitudinal portions, over a limited length, along said tearable surface material lines; and said central longitudinal channel (4, 31, 55) has a cross section which is capable of receiving a tubular element (18) which can be attached to said elongate body, at the junction (13) of said proximal branches (11, 12) of said probe.

2. The probe as claimed in claim 1, wherein said proximal branches (11, 12) are joined to one another, at their junction (13), by joining means (14, 20).

3. The probe as claimed in claim 2, wherein said joining means (20) join said tubular element (18) to said probe.

4. The probe as claimed in claim 1, wherein said flexible and elongate body (2) includes two longitudinal portions (5, 6), and wherein said central longitudinal channel (4) has a cross section in the approximate shape of a lens.

5. The probe as claimed in claim 1, wherein said flexible and elongate body (30) includes three longitudinal portions (32, 33, 34), and wherein said central longitudinal channel (31) has a cross section in the approximate shape of a triangle.

6. The probe as claimed in claim 1, wherein said flexible and elongate body (50) includes four longitudinal portions (51, 52, 53, 54), and wherein said longitudinal channel (55) has a cross section in the approximate shape of a square.

* * * * *